US011083439B2

(12) United States Patent
Chan et al.

(10) Patent No.: US 11,083,439 B2
(45) Date of Patent: Aug. 10, 2021

(54) COOLING UNIT FOR AN ULTRASOUND IMAGING APPARATUS, AND RELATED ULTRASOUND SYSTEMS

(71) Applicant: Clarius Mobile Health Corp., Burnaby (CA)

(72) Inventors: Kwun-Keat Chan, Vancouver (CA); Binda Zhang, Surrey (CA); Daniel Rahardja, Burnaby (CA)

(73) Assignee: Clarius Mobile Health Corp., Vancouver (CA)

( * ) Notice: Subject to any disclaimer, the term of this patent is extended or adjusted under 35 U.S.C. 154(b) by 447 days.

(21) Appl. No.: 15/614,488

(22) Filed: Jun. 5, 2017

(65) Prior Publication Data
US 2018/0344294 A1 Dec. 6, 2018

(51) Int. Cl.
*A61B 8/00* (2006.01)
(52) U.S. Cl.
CPC ............ *A61B 8/546* (2013.01); *A61B 8/4411* (2013.01); *A61B 8/44* (2013.01); *A61B 8/4472* (2013.01)
(58) Field of Classification Search
None
See application file for complete search history.

(56) References Cited

U.S. PATENT DOCUMENTS

| 5,560,362 A * | 10/1996 | Sliwa, Jr. ............... A61B 8/546 600/439 |
| 5,961,465 A * | 10/1999 | Kelly, Jr. ............... A61B 8/546 600/459 |
| 6,362,958 B1 | 3/2002 | Yu et al. |
| 6,542,846 B1 | 4/2003 | Miller et al. |
| 6,709,392 B1 | 3/2004 | Salgo et al. |
| 6,795,314 B1 | 9/2004 | Arbogast et al. |
| 6,980,419 B2 | 12/2005 | Smith et al. |
| 7,948,754 B2 | 5/2011 | Huang |
| 7,998,072 B2 | 8/2011 | Phelps et al. |
| 8,143,898 B1 * | 3/2012 | Markoff ............... A61B 8/4444 324/522 |

(Continued)

FOREIGN PATENT DOCUMENTS

JP 2010088610 A * 4/2010

OTHER PUBLICATIONS

International Search Report and Written Opinion of the International Searching Authority for corresponding PCT International Application No. PCT/CA2018/050632 dated May 30, 2018.

*Primary Examiner* — Angela M Hoffa
*Assistant Examiner* — Younhee Choi
(74) *Attorney, Agent, or Firm* — Julian Ho (57) ABSTRACT

Cooling units for an ultrasound imaging apparatus, and related ultrasound systems are described. The ultrasound imaging systems may include an ultrasound imaging apparatus operable to acquire ultrasound image data; and a cooling unit configured to detachably couple to the ultrasound imaging apparatus. The cooling unit may be cordless and include an active cooling element for removing heat from the ultrasound imaging apparatus. The ultrasound imaging apparatus may have a sensor to determine when the cooling unit is attached. The cooling unit may have an identity interface, and the ultrasound imaging apparatus may use the identity interface to determine whether the cooling unit is compatible.

10 Claims, 7 Drawing Sheets

(56) References Cited

U.S. PATENT DOCUMENTS

| | | |
|---|---|---|
| 8,409,101 B2 | 4/2013 | Hongou et al. |
| 8,475,375 B2 | 7/2013 | Smith et al. |
| 2004/0002655 A1 | 1/2004 | Bolorforosh et al. |
| 2004/0073113 A1 | 4/2004 | Salgo et al. |
| 2004/0179332 A1* | 9/2004 | Smith ................. G01S 7/52082 361/679.41 |
| 2005/0075573 A1 | 4/2005 | Park et al. |
| 2005/0148878 A1 | 7/2005 | Phelps et al. |
| 2006/0082966 A1 | 4/2006 | Lev et al. |
| 2006/0191344 A1* | 8/2006 | Hashimoto .............. A61B 8/00 73/632 |
| 2008/0146924 A1 | 6/2008 | Smith et al. |
| 2009/0261804 A1* | 10/2009 | McKenna .......... A61B 18/1442 324/71.1 |
| 2010/0331702 A1* | 12/2010 | Hongou .................. A61B 8/14 600/459 |
| 2011/0096497 A1 | 4/2011 | Huang |
| 2016/0077059 A1 | 3/2016 | Chung et al. |
| 2016/0242747 A1* | 8/2016 | Siedenburg ............ A61B 8/546 |
| 2017/0020490 A1 | 1/2017 | Ryu et al. |
| 2017/0043189 A1* | 2/2017 | Stoddard .............. A61B 8/4281 |

* cited by examiner

COOLING UNIT FOR AN ULTRASOUND IMAGING APPARATUS, AND RELATED ULTRASOUND SYSTEMS

FIELD

The present disclosure relates generally to ultrasound imaging apparatus, and in particular, a cooling unit for an ultrasound imaging apparatus.

BACKGROUND

Ultrasound imaging systems may generate heat during operation. For example, heat may be generated from the transducer elements in a transducer array when they are activated to transmit ultrasound signals. Also, heat may be generated by integrated circuits (ICs) that drive the transducer array and process imaging data.

When imaging tissue, ultrasound probes (also called ultrasound transducers) are typically placed against the skin of a patient. To prevent patient injury or discomfort due to the probe head having overly high temperatures, there exist regulations that require surfaces of an ultrasound probe to not exceed certain predetermined temperatures while scanning a patient (e.g. International Electrotechnical Commission (IEC) standard 60601 requires external surfaces of an ultrasound probe to not exceed 48° C. in certain conditions).

There are traditional methods of dissipating heat from an ultrasound imaging apparatus. For example, in a traditional wired ultrasound system, heat may be channeled into and through the cable so that it can be dissipated from the cable and/or through the processing body. Heat may also traditionally be dissipated through conduction to the operator and to the patient, and/or through convection to the air. However, during lengthy periods of continuous scanning, these traditional heat mechanisms may not be sufficient.

In addition to adequate heat management, several other considerations may influence the design and operation of an ultrasound imaging apparatus; including ergonomics, battery life, and cleaning.

For example, in a wireless ultrasound imaging apparatus, it may be desirable to minimize the size and weight of the device; maximize operating time; and/or enable simple, quick, effective cleaning. A sealed and/or waterproof enclosure may, for example, enable easier cleaning and sterilization, and/or operation in wet environments. Some traditional wireless ultrasound systems include internal fans or other active cooling elements to increase heat dissipation. However, such traditional systems also typically include slits or vents in the housing to allow airflow caused by the fan. Such slits or vents may make it difficult to clean the ultrasound system without exposing the internal fan or electronics to cleaning fluid that may cause damage to those components.

There is thus a need for improved cooling mechanisms for ultrasound imaging apparatuses. The embodiments discussed herein may address and/or ameliorate at least some of the aforementioned design considerations identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF THE DRAWINGS

Non-limiting examples of various embodiments of the present disclosure will next be described in relation to the drawings, in which.

DETAILED DESCRIPTION

In a first broad aspect of the present disclosure, there is provided an ultrasound imaging system, including: an ultrasound imaging apparatus operable to acquire ultrasound image data; and a cooling unit configured to be detachably coupled to the ultrasound imaging apparatus; wherein the cooling unit includes an active cooling element for removing heat from the ultrasound imaging apparatus, and wherein the cooling unit is cordless.

In some embodiments, the ultrasound imaging apparatus includes a sensor for detecting when the cooling unit is attached. In some embodiments, the sensor includes at least a portion of a resistor network. In some embodiments, the resistor network includes a resistor voltage divider network.

In some embodiments, the ultrasound imaging apparatus includes an external surface and the active cooling element includes a fan, and said fan is configured to direct air onto and/or from said external surface.

In some embodiments, the cooling unit includes at least one fastener to perform the detachable coupling. In some embodiments, the fastener is formed with a housing of the cooling unit. In some embodiments, the housing includes at least one clip portion to provide the detachable coupling.

In some embodiments, the cooling unit is coupled to the ultrasound imaging apparatus using magnetic force. In some embodiments, the cooling unit includes a housing and said housing includes at least one magnet for performing the detachable coupling and wherein a body of the ultrasound imaging apparatus includes a magnetic material for mating with said at least one magnet.

In some embodiments, the ultrasound imaging apparatus provides power to the cooling unit. In some embodiments, the ultrasound imaging apparatus and the cooling unit include connectors configured to mate with one another. In some embodiments, the cooling unit receives power from the ultrasound imaging apparatus.

In some embodiments, the cooling unit is powered independently. In some embodiments, the cooling unit includes a battery for powering the active cooling element.

In some embodiments, the ultrasound imaging apparatus includes a shell, and wherein said shell protects from ingress into an interior of the ultrasound imaging apparatus. In some embodiments, the shell protects of the interior of the ultrasound imaging apparatus from ingress of fluids and dust.

In another broad aspect of the present disclosure, there is provided a method of detecting presence of a compatible cooling unit for attaching to an ultrasound imaging apparatus, the method including: providing a sensor on one of: the ultrasound imaging apparatus, and the cooling unit; providing an identity interface on the other of: the ultrasound imaging apparatus, and the cooling unit; when the cooling unit is attached, the identity interface is read through the sensor; and the attached cooling unit is detected to be compatible if the reading of the identity interface matches an expected reading.

In some embodiments, the method may be considered a method of determining whether a cooling unit is attached to an ultrasound imaging apparatus and/or whether or not it is compatible with said ultrasound imaging apparatus.

In some embodiments, the sensor is provided on the ultrasound imaging apparatus and the identity interface is provided on the cooling unit.

In some embodiments, the ultrasound imaging apparatus includes a first electrical connector capable of supplying current and the cooling unit includes a second electrical connector that interfaces with the first electrical connector. When the cooling unit is attached and determined to be compatible, the ultrasound imaging apparatus activates the first electrical connector to supply electric current to the second connector so that the cooling unit is powered.

In some embodiments, the first electrical connector is prevented from supplying current if the cooling unit is determined to be not compatible. In some embodiments, the ultrasound imaging apparatus is prevented from imaging if the cooling unit is determined to be not compatible.

In some embodiments, the sensor is provided on the cooling unit and the identity interface is provided on the ultrasound imaging apparatus. In some embodiments, the cooling unit is prevented from activating if the cooling unit is determined to be not compatible with the ultrasound imaging apparatus.

In another broad aspect of the present disclosure, there is provided a cooling unit for an ultrasound imaging apparatus, the cooling unit including: a housing, the housing including a fastener for detachably coupling to the ultrasound imaging apparatus; and an active cooling element, wherein the active cooling element is enclosed in the housing, and the active cooling element is configured to remove heat from the ultrasound imaging apparatus; wherein the cooling unit is cordless.

In some embodiments, the active cooling element includes a fan configured to direct air onto or away from an external surface of the ultrasound imaging apparatus.

In some embodiments, the cooling unit housing includes at least one air inlet and at least one air outlet. In some embodiments, a size of the air inlet is different (e.g., larger) from the size of the air outlet to induce a pressure differential.

In some embodiments, the cooling unit includes an electrical connector for receiving power from the ultrasound imaging apparatus to power the active cooling element.

In some embodiments, the cooling unit includes an internal battery for providing power to the active cooling element.

In some embodiments, the fastener is formed with the housing, and the housing includes at least one clip for performing the detachable coupling.

In some embodiments, the housing includes at least one magnet for performing the detachable coupling and the ultrasound imaging apparatus includes a portion of the body for mating with the at least one magnet.

In some embodiments, the cooling unit is waterproof allowing for, for example, cleaning with liquids.

In some embodiments, the cooling unit is dustproof allowing for operation in environments with small particles which may negatively affect the performance of the cooling unit.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

Figure 1:
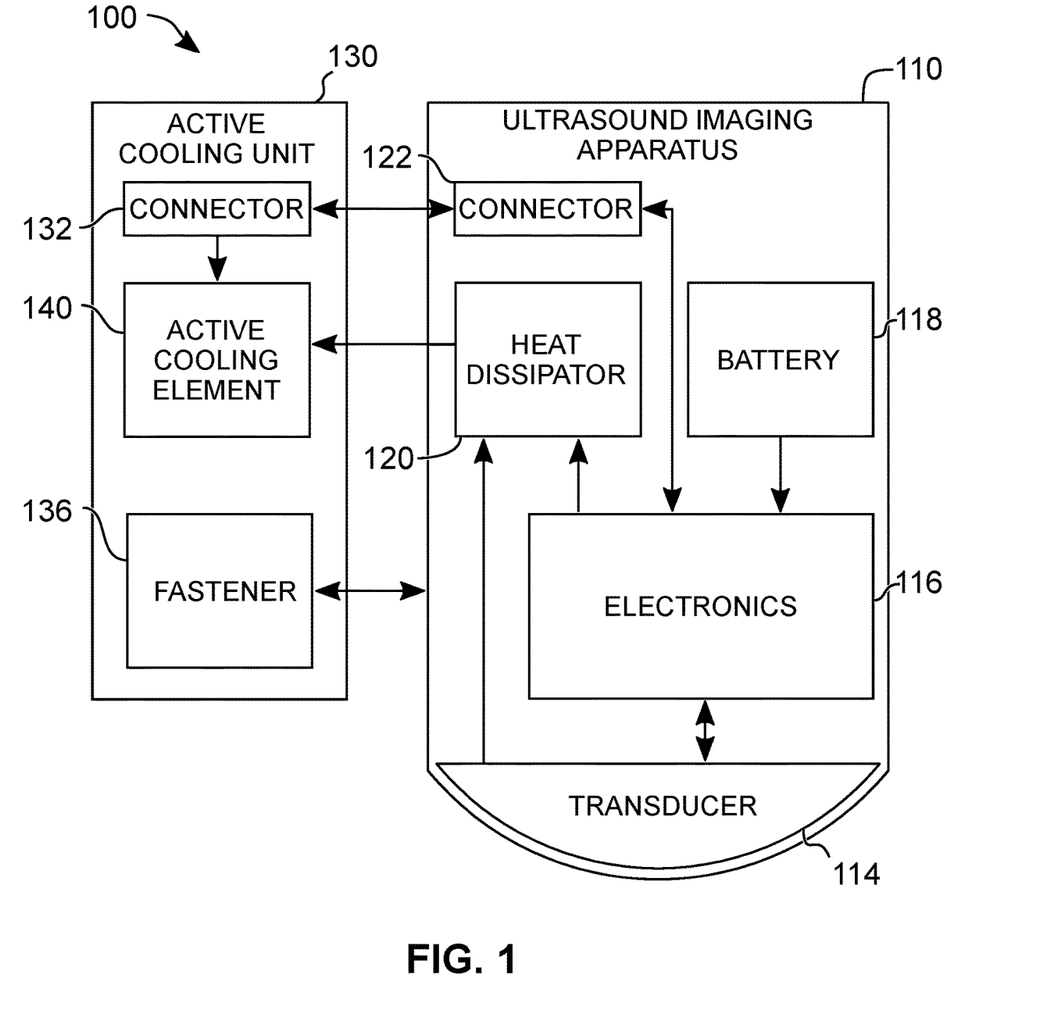
FIG. 1 shows a schematic representation of an ultrasound system, in accordance with at least one embodiment of the present invention.

Referring to FIG. 1, shown there generally as 100 is a schematic representation of an ultrasound imaging system, in accordance with at least one embodiment of the present invention. As shown, the ultrasound imaging system includes an ultrasound imaging apparatus 110 and an active cooling unit 130 that can detachably couple to the ultrasound imaging apparatus 110.

The ultrasound imaging apparatus 110 may contain a transducer 114 which may be configured to emit ultrasound energy signals towards an object and receive echoes of the ultrasound energy signals that reflect off the object. Transducer 114 may be electrically connected to electronics 116 which can control the transducer 114 and process the received echoes into ultrasound image data. Ultrasound imaging apparatus 110 may have a battery 118 for providing power to the electronics 116. Ultrasound imaging apparatus 110 may have a heat dissipater 120 that receives heat from the electronics 116 and/or transducer 114 and/or battery 118 during operation. Active cooling unit 130 may include a fastener 136 for facilitating the detachable physical coupling of the active cooling unit 130 to the ultrasound imaging apparatus 110. When it is attached, active cooling unit 130 can be configured to remove heat from the ultrasound imaging apparatus' heat dissipater 120 using active cooling element 140. Active cooling unit 130 may include a connector 132 that electrically connects to the corresponding connector 122 on the ultrasound imaging apparatus 110 when the active cooling unit 130 is coupled to ultrasound imaging apparatus 110. In various embodiments, connector 132 may serve different purposes. For example, the electrical connection between connector 132 and connector 122 may enable ultrasound imaging apparatus 110 to provide power to active cooling element 140, and/or enable ultrasound imaging apparatus 110 to determine when a compatible active cooling unit 130 is attached.

During operation, ultrasound imaging apparatus 110 may transmit ultrasound image or other data to a tertiary device for display or storage. For example, ultrasound imaging apparatus 110 may transmit data via a wired or wireless connection to a multi-use electronic display device to display an ultrasound image.

In various embodiments, the cooling unit 130 may generally be provided in a cordless form that can operate without attached wires or cords (e.g., either for supplying power or for transferring heat away from the cooling unit 130). Corded devices may generally be cumbersome to use, and the cooling unit 130 being cordless may provide enhanced ease of use.

Figure 2A:
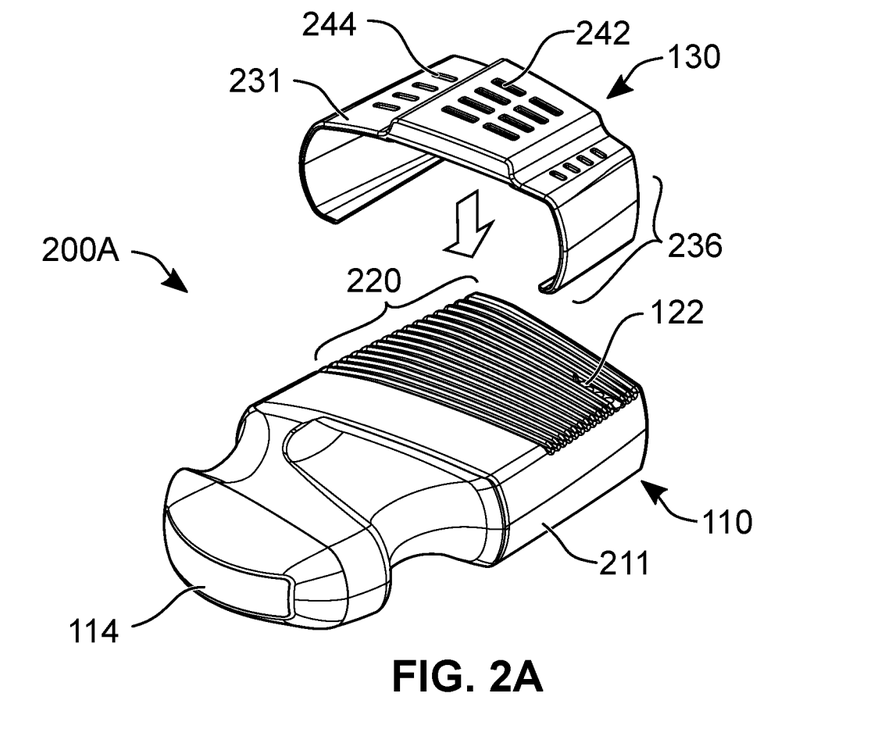
FIG. 2A-2B shows a perspective view of an ultrasound imaging system with an active cooling unit in a detached state and an attached state, respectively, in accordance with at least one embodiment of the present invention.
Figure 2B:
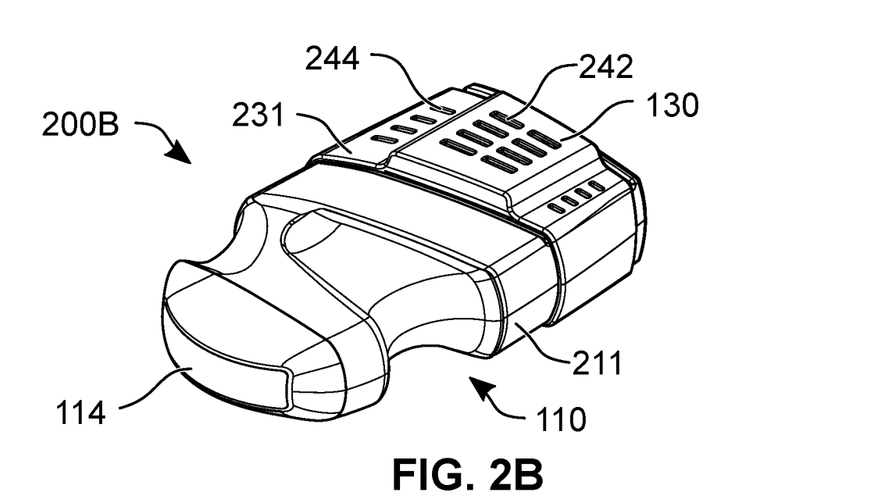

Referring to FIG. 2A and FIG. 2B, shown there generally as 200A and 200B, respectively, are perspective views of an example embodiment of an ultrasound imaging system, in accordance with at least one example embodiment of the present invention. FIG. 2A shows ultrasound imaging system 200A with ultrasound imaging apparatus 110 and active cooling unit 130 in a detached state. FIG. 2B shows the same ultrasound imaging system 200B, with ultrasound imaging apparatus 110 and active cooling unit 130 in an attached state.

The ultrasound imaging apparatus 110 generally has a shell 211 which may be connected to a transducer array 114 and, internal to the shell, the processing components. As the ultrasound imaging apparatus 110 is used to perform imaging, heat may be generated by the transducer array 114 and/or the processing components (e.g., the electronics 116 shown in FIG. 1) and/or the battery 118. As shown in FIG. 2A, a heat dissipater 120 shown in FIG. 1 is provided as fins 220 on the shell 211 of the ultrasound imaging apparatus 110. The fins 220 help to passively dissipate heat from the ultrasound imaging apparatus 110 using natural convection. While fins 220 may generally provide a sufficient level of heat dissipation, it may be desirable to further enhance the heat dissipation in certain circumstances. For example, further enhancing the heat dissipation may allow for continuous scanning by the ultrasound imaging apparatus 110 over a lengthy period.

To increase the heat dissipated from ultrasound imaging apparatus 110, active cooling unit 130 may be attached (as shown in FIG. 2B). Active cooling unit 130 generally has a main body 231, and may also include a fastener for detachably coupling the active cooling unit 130 to the ultrasound imaging apparatus 110. In the example embodiment of FIGS. 2A-2B, the fastener is formed with the main body 231 as a clip portion 236 that facilitates attachment of the cooling unit 130 to the ultrasound imaging apparatus 110. The main body 231 may also include air inlets 242 and air outlets 244 to allow air to flow past and/or through the active cooling element (not shown in FIGS. 2A and 2B).

In this illustrated embodiment, cooling unit 130 attaches to ultrasound imaging apparatus 110 using a fastener provided in the form of clip portion 236. Clip portion 236 can be made of a suitably flexible material to allow the clip portion 236 to flex around/over the shell 211 and snap on/off of the ultrasound imaging apparatus 110. In various embodiments, the material of clip portion 236 and/or the main body 231 of the cooling unit 130 may be selected to provide additional heat conduction from shell 211 to active cooling unit 130. The coupling mechanism may be releasable without the use of tools, as is the case with the example flexible clip portion 236. However, in some embodiments, the use of tools for releasing the cooling unit 130 may be possible.

In some embodiments, the coupling mechanism (e.g., the fastener) may be configured to maintain a specific relative position between the active cooling unit 130 and the ultrasound imaging apparatus 110. This may facilitate improved heat transfer over embodiments without such relative positioning. For example, as illustrated, the clip portion 236 may be shaped to match the profile of a portion (e.g., shell 211) of the ultrasound imaging apparatus 110. The matching of the clip portion 236 to one or more of the profile, shape, and/or curvature of the shell 211 may allow the cooling unit 130 to be positioned substantially over the fins 220 so that the active cooling element can operate primarily thereon. This, in turn, may enhance the heat dissipated from the fins 220.

Figure 3:
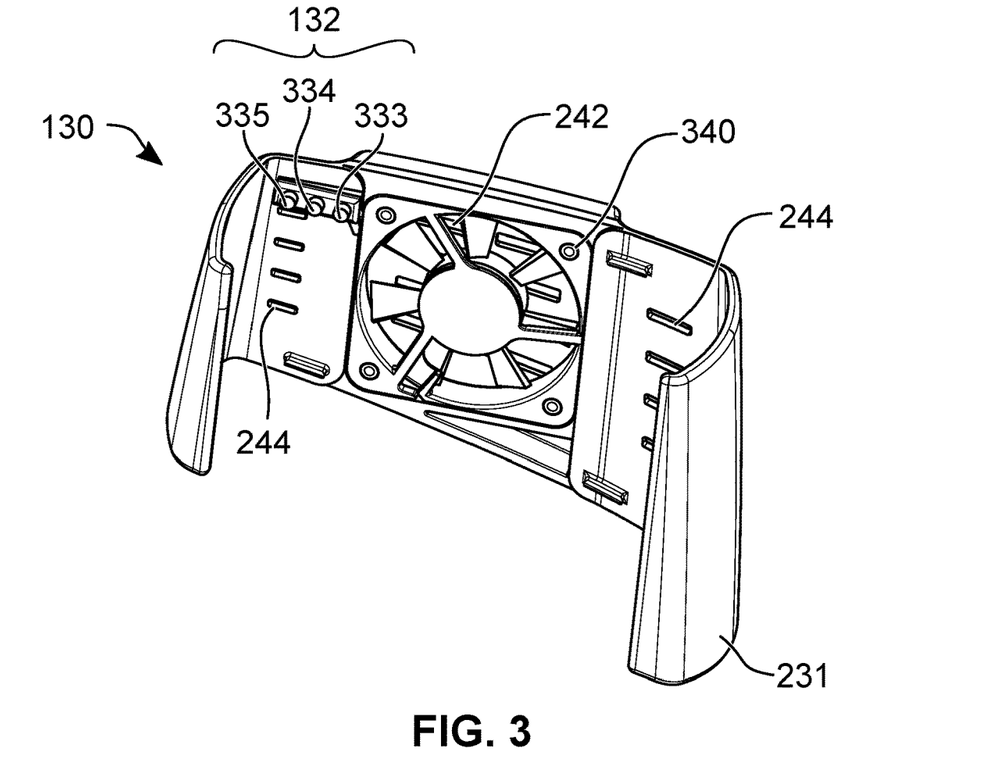
FIG. 3 shows a rear perspective view of the active cooling unit of FIG. 2A-2B, in accordance with at least one embodiment of the present invention.

Referring to FIG. 3, shown there generally as 230 is a rear perspective view of an active cooling unit 130, in accordance with at least one embodiment of the present invention. As noted with respect to FIG. 1, the active cooling unit 130 may include an active cooling element 140. In the example embodiment shown in FIG. 3, the active cooling element 140 is provided in the form of a fan 340 mounted to the main body 231.

Connector 132 can also be mounted to main body 231, and may form an electrical connection to the fan 340. As discussed below, connector 132 may include several pins 334, 335, and 336 that can provide power to the fan and/or provide access to an identity interface when attached to the ultrasound imaging apparatus 110. The at least one air inlet 242 and at least one air outlet 244 formed as holes in the housing 231 of the cooling unit 130 are also viewable in FIG. 3.

Figure 4:
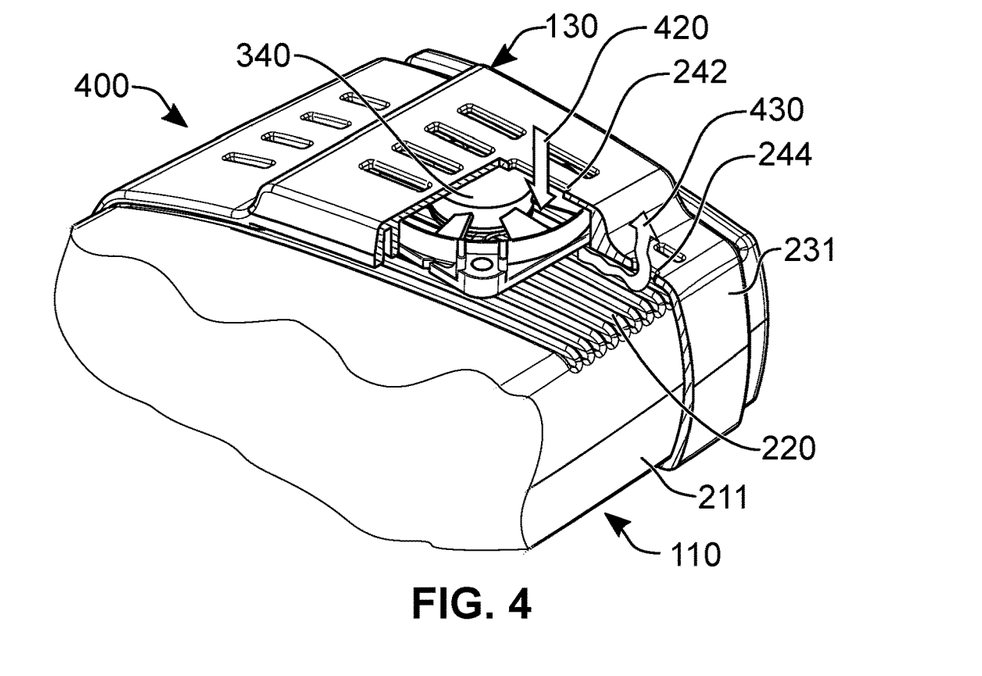
FIG. 4 shows a partial break-out section view of the ultrasound imaging system when the cooling unit is attached, in accordance with at least one embodiment of the present invention.

Referring to FIG. 4, shown there generally as 400 is a partial perspective view of the ultrasound imaging system of FIG. 2 with a broken-out section to show example airflow. During operation, cool air can be drawn into active cooling unit 130 through air inlets 242 along air inlet path 420 by fan 340. Once through fan 340, air can be directed into and along the fins 220 of the ultrasound imaging apparatus 110. Heat can then be transferred from the fins 220 to the cool air through convection. The warm air may then continue to travel along air outlet path 430 through the air outlet 244 in housing 231 and into the surrounding environment. In this embodiment, the cool air can be directed onto the surface of the heat dissipater 120 (e.g., fins 220) to generate more turbulence and enhance heat transfer. It can be appreciated that those skilled in the art may choose to use a different air pathway. For example, the fan may be configured to operate so that airflow is in the reverse direction so as to draw air away from an external surface of the ultrasound imaging apparatus 110.

In some embodiments, the size and shape of air inlets 242 and air outlets 244 can be configured so that the air inlets 242 are different from the air outlets 244 (e.g., as shown, the air inlets 242 are larger than the air outlets 244). Such a configuration may create a pressure differential across the fan 340, so as to increase the pressure (and thus velocity) of the airflow downstream from the fan 340 directed at the fins 220. This, in turn, may improve heat dissipation performance. In various embodiments, the location of air inlets 242 and air outlets 244 may be chosen to direct the warm air away from the operator of the ultrasound imaging apparatus 110 and/or away from the patient during scanning.

Figure 5:
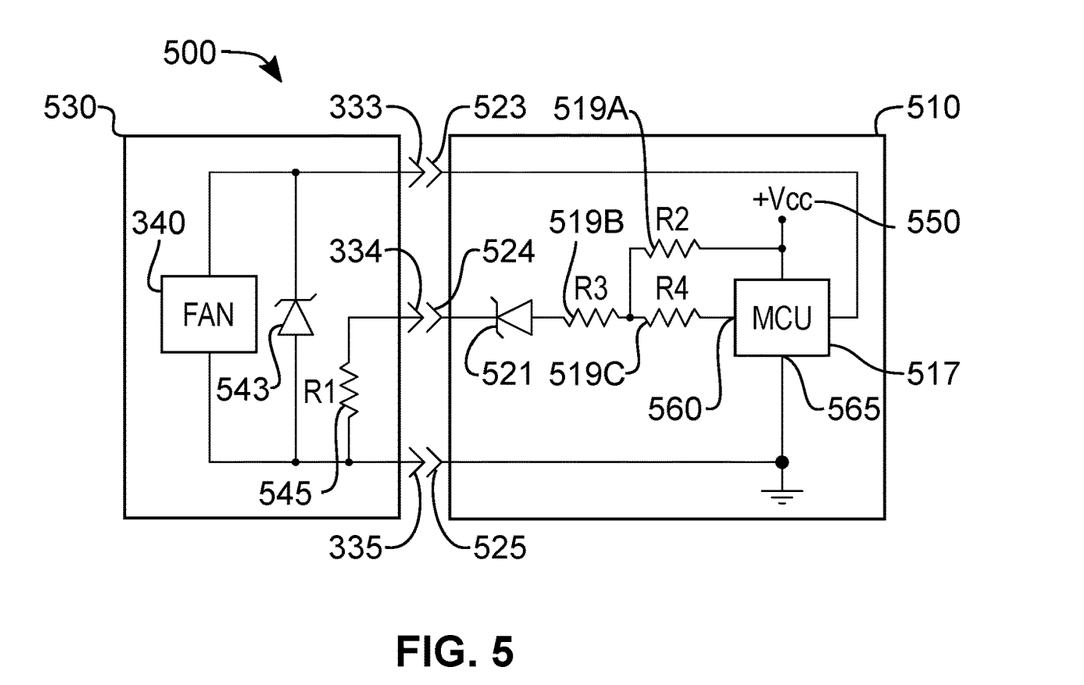
FIG. 5 shows an electrical schematic of some of the components of the ultrasound imaging system of FIG. 2A-2B, in accordance with at least one embodiment of the present invention.

Referring to FIG. 5, shown there generally as 500 is an electrical schematic for active cooling unit 130 of the ultrasound imaging system of FIGS. 2A-2B. The electrical schematic includes an ultrasound imaging apparatus portion 510 and an active cooling unit portion 530. The apparatus portion 510 and the active cooling unit portion 530 can be connected via pins 333, 334, 335 on the active cooling unit portion 530 and corresponding pins 523, 524, 525 on the apparatus portion 510. Each of the apparatus pins 523, 524, 525 may be connected to a processor 517 (e.g., microcontroller unit (MCU)). As discussed below, when the cooling unit portion 530 is attached to the apparatus portion 510, processor 517 may control the flow of electricity to the fan 340 and/or detect whether a cooling unit 130 encompassing the attached fan portion 530 circuit is compatible.

The electrical schematic of FIG. 5 may operate in a detached state and an attached state, and processor 517 can be configured to determine in which state the circuit is operating. In the detached state, pins 333, 334, and 335 are not electrically connected to target pins 523, 524, and 525, respectively. In the attached state, pins 333, 334, and 335 are electrically connected to target pins 523, 524, and 525, respectively.

Processor 517 may be configured to control power to fan 340 and therefore control when the fan 340 operates. Processor 517 may be connected to target pin 523 on apparatus portion 510, and fan 340 may be connected to pin 333 on cooling unit portion 530. In the attached state, pin 333 and target pin 523 are electrically connected. Processor 517 can then activate power to target pin 523 so that current flows through pin 333 to energize fan 340. In this mode of operation, pin 523 may be a live or hot pin that supplies current to the fan 340 through pin 333, and pin 525 may be the neutral pin that returns current to the processor 517 through pin 335 connected to fan 340. In the detached state, processor 517 may deactivate power to target pin 523 and prevent electric current from flowing thereto. In some embodiments, processor 517 activates the fan 340 whenever the active cooling unit 130 is determined to be attached.

A processor 517 may determine whether a compatible cooling unit 130 is attached in various ways. For example, as illustrated, the compatible cooling unit 130 may include the cooling unit portion 530 of the circuit shown in FIG. 5. Detector pin 524 may be provided on the apparatus portion 510 that, in the attached state, mates with a corresponding identity pin 334 on the cooling unit portion 530 to form an electrical connection. The electronics between detector pin 524 and neutral pin 525 connected within the apparatus portion 510 (e.g., including processor 517 and voltage source 550 (labeled as '+Vcc')) may be considered circuitry for detecting the presence of a cooling unit 130. In the illustrated embodiment, this detection circuitry includes a first portion of a voltage divider circuit, having resistor 519A (labeled as 'R2'), resistor 519B (labeled as 'R3'), and resistor 519C (labeled as 'R4').

In operation, the processor 517 may be configured to measure voltage in the detection circuitry at regular intervals to determine whether a compatible cooling unit portion 530 is attached. For example, in the detached state, there is typically no electrical connection between detector pin 524 and neutral pin 525 on the apparatus portion 510. This would result in significant resistance across those two pins, such that current is unlikely to flow through resistor 519B from the voltage source 550. As a result, current will generally flow from the voltage source 550 through resistor 519A towards resistor 519C so as to produce a first predetermined voltage measurement between the connection point 560 and connection point 565 (This first predetermined voltage measurement would depend on the resistance of the resistors 519A, 519C). If a measured voltage that is taken periodically matches this first predetermined voltage measurement, the processor 517 may determine that a compatible cooling unit 530 is not attached. For example, the processor 517 may then substantially limit the flow of current towards the pin 523 from voltage source 550.

As illustrated, active cooling unit portion 530 may include a second portion of a voltage divider circuit having resistor 545. When the active cooling portion 530 is attached, an electrical connection may be formed between detector pin 524 and neutral pin 525 on the apparatus portion 510 (e.g., through identity pin 334, resistor 545, and pin 335 on the cooling unit portion 530). This electrical connection may complete the voltage divider circuit, and draw current towards resistor 519B at the connection point between resistor 519A and resistor 519C. Current may then flow through resistor 545, and back towards connection point 565 at processor 517. Since some current has been divided away from the circuit having resistors 519A and 519C, a voltage measurement taken across connection points 560 and 565 will be different from the first predetermined voltage measurement when there was no cooling unit portion 530 attached and there was substantial resistance across target pins 524 and 525. The resistance of the resistor 545 on the cooling unit portion 530 may be selected so that when the cooling unit portion 530 is attached, a predetermined voltage at connection point 560 is experienced. In various embodiments, if the periodically measured voltage matches a second predetermined voltage across the connection point 560 and connection point 565 (e.g., the amount of voltage divided away from the first predetermined voltage measurement is consistent with that which is expected based on the expected resistance provided by resistor 545), then the processor 517 may determine that a compatible cooling unit 545 is attached.

However, if the electrical circuit between detection pin 524 and neutral pin 525 is complete, but the measured voltage does not match the second predetermined voltage (e.g., the amount of voltage divided away from the first determined voltage measurement above is inconsistent with an expected resistance of resistor 545 based on the design of a compatible cooling unit portion 530), the processor 517 may determine that an incompatible cooling unit 130 is attached. To facilitate ease of manufacturing and/or ease of sourcing of components, the second predetermined voltage may include different resistance values corresponding to different resistors, so that if the measured voltage matches any one of these different resistance values, the attached cooling unit portion 530 may be determined to be compatible.

In another scenario, it may be possible that target pin 524 and target pin 525 on the apparatus portion 510 are shorted such that there is little to no resistance experienced between the two pins. For example, this may happen if the ultrasound imaging apparatus 110 is submerged in water or other conductive liquid during cleaning. This may result in another predetermined voltage experienced across: either voltage source 550 and connection point 560, or between connection points 560 and 565. If any voltage measurement matches such predetermined voltage, then the processor 517 may also determine that a compatible cooling unit 130 has not been attached, so as to also substantially limit the flow of current towards pin 523 from voltage source 550.

In various embodiments, when determining whether a measured voltage matches a predetermined voltage, the processor 517 may not necessarily identify a precise voltage. Instead, if a measured voltage is within a known variance of the predetermined voltage (e.g., within an expected range based on component specifications), the measured voltage may still be considered as matching. For example, when selecting the lower and upper bounds of an expected voltage range, the next lower and next higher standard values of resistors may be taken into account. For an example target resistance of 2K ohms, the adjacent standard values in the IEC 60063 E96 series are 1.96K ohms and 2.05K ohms. Thus, these values may be selected to be the lower and upper bounds of an expected voltage range if the 2K ohm resistor is selected as resistor 545 to be placed into a compatible cooling unit 130.

In the manner discussed, the resistance of resistor 545 may serve as an identity interface that allows the apparatus portion 510 to determine whether an attached cooling unit portion 530 is compatible. For example, the reading of the identity interface by the apparatus portion 510 may facilitate detection of counterfeit and/or malfunctioning cooling units 130. Since such non-compatible cooling units 130 may not be configured to safely handle the electrical current supplied via live pin 523 when pin 523 is activated, the processor 517 may be configured to only activate current flow to pin 523 if an attached cooling unit 130 is determined to be compatible. This may provide enhanced safety and reduce the possibility of electric shock. As discussed below, this may also allow the pins 523, 524, 525 to be exposed to liquids such as water when cleaning the ultrasound imaging apparatus.

As discussed above, the processor may use the identify interface on the cooling unit portion 530 to determine when to supply power to pin 523 for activating the fan 340. However, in some embodiments, processor 517 may use additional or alternative information to determine when to supply power to pin 523. For example, the processor 517 may activate or deactivate current flow to pin 523 based on a current imaging mode of the ultrasound imaging apparatus 110; a temperature measured within the ultrasound imaging apparatus 110; and/or based on input from the operator.

In some embodiments, the circuit may include protective circuitry. For example, as shown in the example circuit of FIG. 5, a snubber diode 543 is connected in reverse parallel with fan 340 to prevent inductive kickback. As shown in FIG. 5, a diode 521 is also connected to detector pin 524 to prevent current flow towards connection point 560 in a manner that may potentially result in an erroneous determination that a compatible cooling unit 130 has been attached. Various other embodiments may also include components to prevent damage to the ultrasound imaging apparatus 110 from electrostatic discharge or unexpected connections.

As discussed herein, the detection circuitry provided on the apparatus portion 510 may be considered a sensor that reads the identity interface provided on the cooling unit 130. In various embodiments, other types of sensors may be used to determine whether a compatible active cooling unit 130 is attached to the ultrasound imaging apparatus 110. For example, the sensor may include a mechanical switch, a magnet and reed switch, and/or a radio frequency identification (RFID) tag. Other known or later developed sensors capable of detecting the attachment of the active cooling unit can be used.

Figure 6:
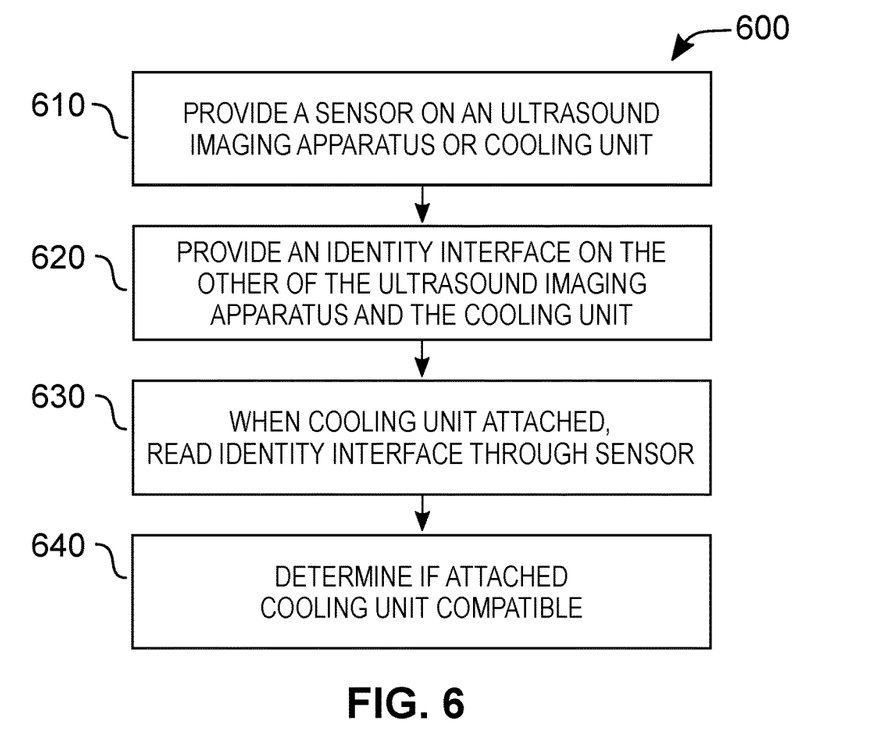
FIG. 6 is a flowchart diagram showing steps of a method for determining whether an active cooling unit is attached to and compatible with an ultrasound imaging apparatus, in accordance with at least one embodiment of the present invention.

Referring to FIG. 6, shown there generally as 600 is a flow chart depicting a method for determining whether an attached active cooling unit is compatible with an ultrasound imaging apparatus, according to at least one embodiment of the present invention. The method may be performed by the ultrasound imaging apparatus 110. Alternatively, the method may be performed by the active cooling unit 130.

At 610, a sensor may be provided on an ultrasound imaging apparatus 110 or an active cooling unit 130. The sensor may be any suitable component or combination of components that allows for reading an identity interface. For example, as noted, the portion of the detection circuit like that which is provided on the apparatus portion 510 (e.g., including a portion of a voltage divider circuit and processor 517) may be considered a sensor.

At 620, an identity interface may be provided on the other of the active cooling unit 130 and the ultrasound imaging apparatus 110. The identity interface may be any component (or combination of components) that allows a corresponding sensor to determine whether a cooling unit 130 is compatible. For example, in the detection circuitry of FIG. 5, the identity interface includes a resistor 545 with a predetermined resistance that completes the voltage divider circuit in the sensor when the cooling unit 130 having the cooling unit portion 530 is attached to the apparatus portion 510.

At 630, the sensor may read the identity interface when the active cooling unit 130 is attached to the ultrasound imaging apparatus 110. The reading of the identity interface may be performed in various ways. For example, in the example embodiment of FIG. 5 where the sensor is a portion of a voltage divider circuit, the reading may be performed by a processor 517 taking periodic voltage measurements as discussed above. When the cooling unit 130 is attached, a voltage at connection point 560 can be read and compared with a predetermined value.

At 640, the compatibility of the active cooling unit 130 is determined. Compatibility may be determined in various ways. For example, determining compatibility may involve comparing a value read at act 630 with one or more predetermined values. As discussed above, in example embodiment where the identity interface includes a resistor 545, these predetermined values may be an expected range of resistance values for resistors that have been selected for inclusion in compatible cooling units 130. In the manner discussed, the identity interface may serve to "identify" the cooling unit 130 to the imaging apparatus 110. This may help ensure any attached cooling unit 130 used with the imaging apparatus 110 is not counterfeit and/or has met sufficient quality and safety standards.

If the active cooling unit 130 is determined to be incompatible, one or more different actions may be taken. For example, the operator may be alerted. Additionally or alternatively, if the active cooling unit 130 would normally receive power from the ultrasound imaging apparatus 110 through an electrical connection, the power may be disabled. Additionally or alternatively, the ultrasound imaging apparatus 110 may be prevented from imaging.

If the active cooling unit is determined to be compatible, one or more other actions may be taken. For example, as noted, the ultrasound imaging apparatus 110 may provide electrical power through an electrical connection to power and activate the active cooling unit 130. If the active cooling unit 130 is independently powered, the ultrasound imaging apparatus may instruct the active cooling unit 130 to begin cooling.

While the illustrated embodiment provides an identity interface in the form of a resistor 545 being part of a voltage divider circuit (with the corresponding sensor being the remaining portion of the voltage divider circuit), different embodiments may provide an identity interface and corresponding sensor in various ways. For example, any combination of electrical, mechanical, digital, optical, wireless, or software-based components can be provided as an identity interface, and a suitable sensor may be used for identifying the identity interface and determining compatibility. Also, as illustrated herein, the sensor is provided on the ultrasound imaging apparatus 110 and the identity interface is provided on the cooling unit 130. However, in various embodiments, the positioning of these elements may be reversed: e.g., the sensor may be provided on the cooling unit 130, and the identity interface may be provided on the imaging apparatus 110.

Although the cooling units discussed herein have generally referred to active cooling units, the methods of FIG. 6 may also be performed on passive cooling units in various embodiments. A passive cooling unit may dissipate heat without the need for electrical energy. For example, cooling unit 130 may include a heat sink thermally connected to a heat transfer surface. The heat transfer surface may be configured to thermally mate with the heat dissipating portion 120 of the imaging apparatus 110, so that heat from the imaging apparatus 110 is transferred to the heat sink and dissipated. In another example, cooling unit 130 may include a heat storage device to temporarily store heat from the imaging apparatus 110. As discussed herein, detecting the compatibility of a passive cooling unit may allow the ultrasound imaging apparatus to modify its operation (e.g., allow/disallow imaging, and/or modifying imaging parameters).

Figure 7A:
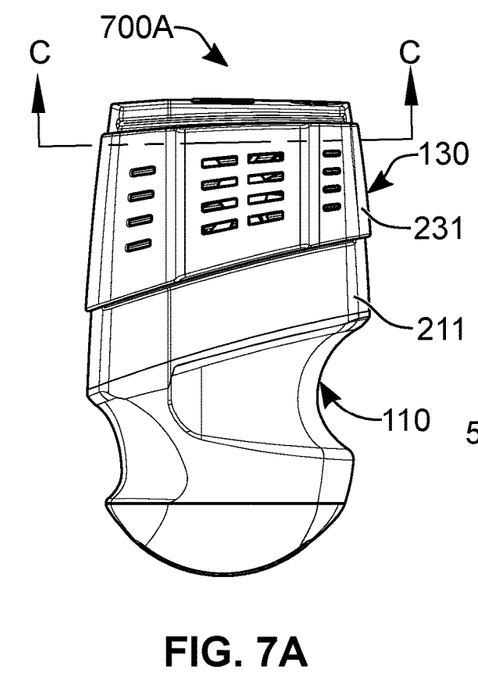
FIG. 7A shows a front view of the ultrasound imaging system of FIGS. 2A-2B, in accordance with at least one embodiment of the present invention.

Referring to FIG. 7A, shown there generally as 700A is a front view of the ultrasound imaging system of FIGS. 2A-2B. The connector 122 on ultrasound imaging apparatus 110 may have target pins 523, 524, 525 (as discussed above in relation to FIG. 5). In various embodiments, these target pins 523, 524, 525 may be provided in the form of exposed electrical pads that can be powered when a cooling unit 130 is attached. Having such exposed electrical connection points may potentially result in risk of electric shock if the pins become powered unexpectedly. As noted above, configuring the pins to detect that a cooling unit 130 is compatible prior to powering the pins may enhance safety and reduce the risk of electric shock.

Additionally, having exposed electrical connection points may traditionally make it more difficult to clean or sterilize the ultrasound imaging apparatus 110. This is because having exposed electrical connections may require openings to be provided on the external shell 211. In turn, these openings may potentially allow a cleaning agent (e.g., water or other disinfectant liquid) to ingress into the interior of the ultrasound imaging apparatus 110 to damage the electronics contained therein. Notwithstanding these challenges, in some embodiments of the present invention, the construction of the exposed electrical connections through shell 211 may protect from ingress of fluid and dust into the interior of ultrasound imaging apparatus 110. For example, in various embodiments, the shell 211 may satisfy an International Electrotechnical Commission (IEC) rating of at least IPX7.

Figure 7B:
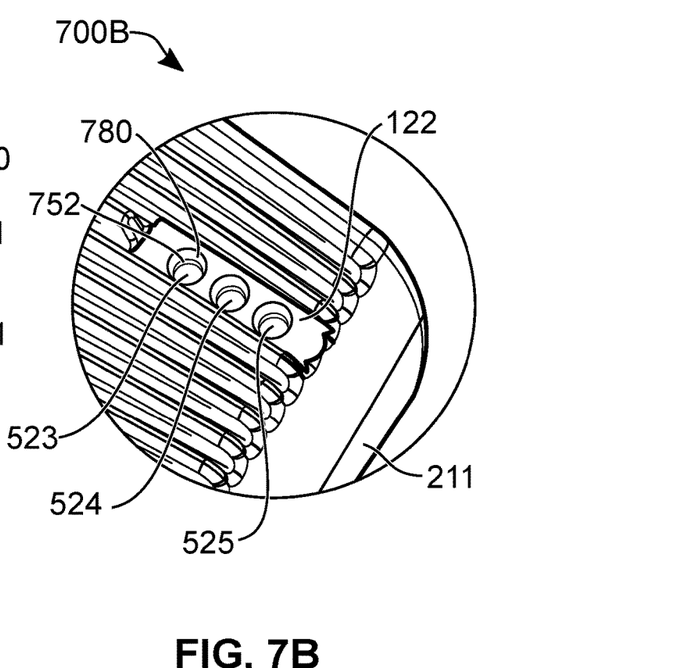
FIG. 7B shows an enlarged partial perspective view of the connector of the ultrasound imaging apparatus of FIGS. 2A-2B, in accordance with at least one embodiment of the present invention.

Referring to FIG. 7B, shown there generally as 700B is an enlarged partial perspective view of the connector 122 of the ultrasound imaging apparatus 110 of FIGS. 2A-2B. As shown in FIG. 7B, the openings 780 in the shell 211 providing access to the electrical pads 523, 524, 525 of connector 122 may be sealed from the interior of the ultrasound imaging apparatus 110 via waterproof tape 752. In an example embodiment, one or more hole(s) may be cut in the waterproof tape 752 so that the hole(s) expose corresponding electrical pads 523, 524, 525. One side of the tape may be adhered to a printed circuit board (PCB) having the electrical pads 523, 524, 525 that can mate to pins 333, 334, 335 of the active cooling unit 130; and the other side of the tape 752 may be adhered to the interior surface of the shell 211 (either directly or indirectly through another medium that provides sealing and still exposes the electrical pads). This may allow the electrical pads 523, 524, 525 to be exposed through the waterproof tape 752 and the shell 211 while maintaining ingress protection of liquids and other materials into the interior of the ultrasound imaging apparatus 110.

Figure 7C:
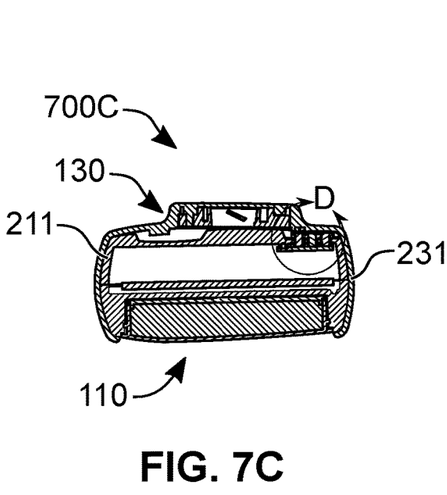
FIG. 7C shows a cross-sectional view of the ultrasound imaging system of FIG. 2A-2B along line C-C shown in FIG. 7A, in accordance with at least one embodiment of the present invention.

Referring to FIG. 7C, shown there generally as 700C is a cross-sectional view of the ultrasound imaging system of FIG. 2A-2B along line C-C show in FIG. 7A, in accordance with at least one embodiment of the present invention. In the cross-sectional view of FIG. 7C, the cooling unit 130 is attached to the ultrasound imaging apparatus 110, with the clip portion of the cooling unit 130's main body 231 fitting around the outer shell 211 of the ultrasound imaging apparatus 110.

Figure 7D:
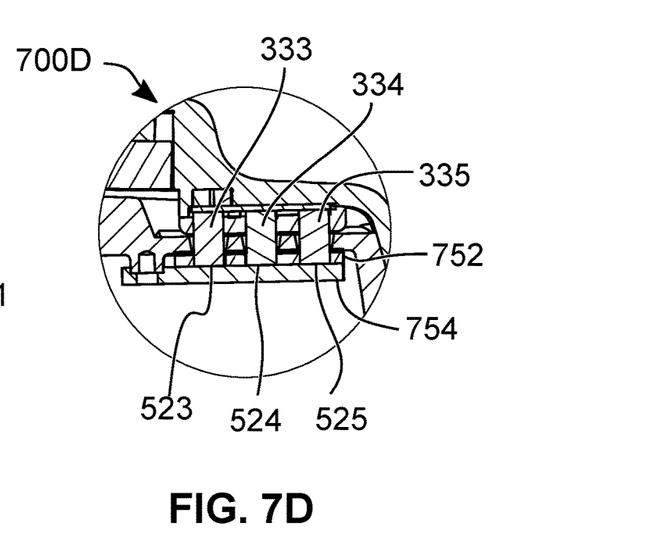
FIG. 7D shows a detail view drawn from FIG. 7C of the ultrasound imaging system of FIG. 2A-2B, in accordance with at least one embodiment of the present invention.

Referring to FIG. 7D, shown there generally as 700D is a detail view of the area highlighted by 'D' in FIG. 7C, in accordance with at least one embodiment of the present invention. In this view, the waterproof tape 752 is viewable. The lower side of the waterproof tape 752 is adhered to the PCB 754 having the electrical pads 523, 524, 525 and the upper side of the waterproof tape 752 is adhered to the interior of the interior surface of the shell 211. The pins 333, 334, 335 may penetrate the holes in the waterproof tape 752 to mate with the exposed electrical pads 523, 524, 525, and form an electrical connection therewith. In various embodiments, one or more pins 333, 334, 335 may be provided as spring-loaded pins. For example, this may allow for a solid electrical connection by providing secure contact between the pin and the exposed electrical pads. For example, one option for spring-loaded pins is POGO™ pins from Everett Charles Technologies. In various embodiments, the spring-loaded pins and the target exposed pads should be chosen of a material that is suitable for immersion in a cleaning or disinfection solution.

Various embodiments discussed herein may configure the ultrasound imaging apparatus 110 to be protected from ingress. As discussed, this may facilitate ease of cleaning (e.g., allow for wiping with disinfection solution and/or allow for the ultrasound imaging apparatus 110 to be submersed in liquid). The embodiments may be configured to maintain this ingress protection even with exposed electrical connectors that mate with electrical connectors from the cooling unit 130.

In the example embodiment shown in FIG. 7A-7C, waterproof tape 752 is discussed as providing the sealing mechanism that provides ingress protection. However, it will be understood that other suitable methods (e.g., other types of mechanical fasteners, sealants, gaskets, O-rings) for providing ingress protection while still providing exposed electrical connectors may be possible.

Figure 8:
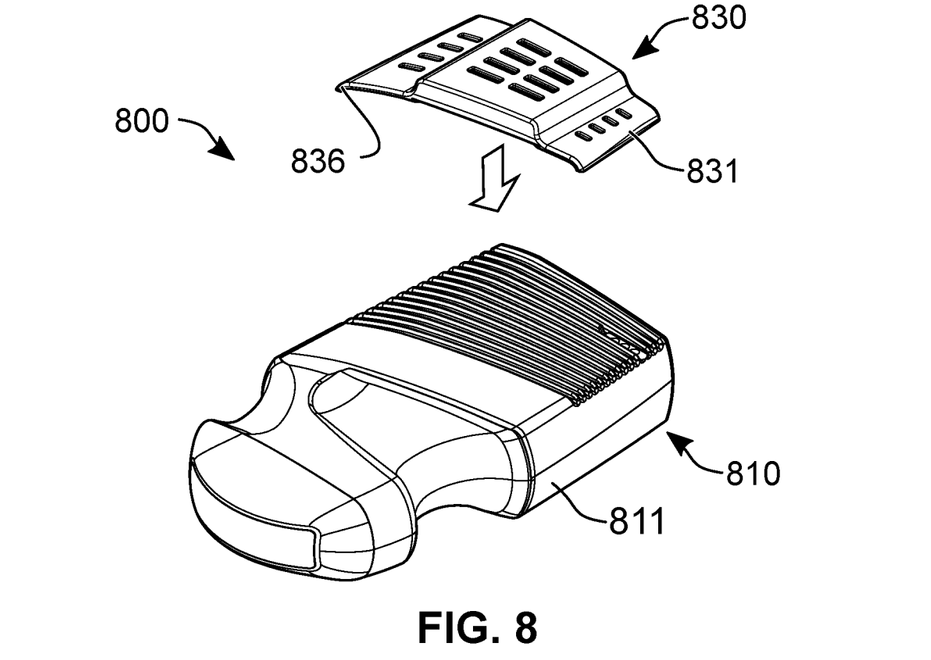
FIGS. 8-11 show perspective views of various alternative configurations of an ultrasound imaging system, in accordance with various embodiments of the present invention.

Referring to FIG. 8, shown there generally as 800 is a perspective view of an embodiment of the present invention, with an alternative means of coupling the active cooling unit to the ultrasound imaging apparatus. Ultrasound imaging system 800 may include an ultrasound imaging apparatus 810 and a detachable active cooling unit 830. Active cooling unit 830 may have a housing 831 configured with at least one magnet 836. The at least one magnet 836 may couple to shell 811, and thereby allow fastening of the detachable active cooling unit 830 to the ultrasound imaging apparatus 810. In various embodiments, different arrangements of magnets could be used. For example, permanent magnets could be attached onto both the cooling unit housing 831 and ultrasound imaging apparatus shell 811. Alternatively, permanent magnets could be attached to one of the cooling unit 830 or the ultrasound imaging apparatus 810; with the other component being formed with a magnetically responsive material, so as to allow a magnetic connection to be formed therebetween (e.g., mating between the cooling unit 830 and the ultrasound imaging apparatus 810). In some embodiments, the orientation of the magnets coupled with different polarities provide the ability to align the cooling unit 830 to the ultrasound imaging apparatus 810.

Figure 9:
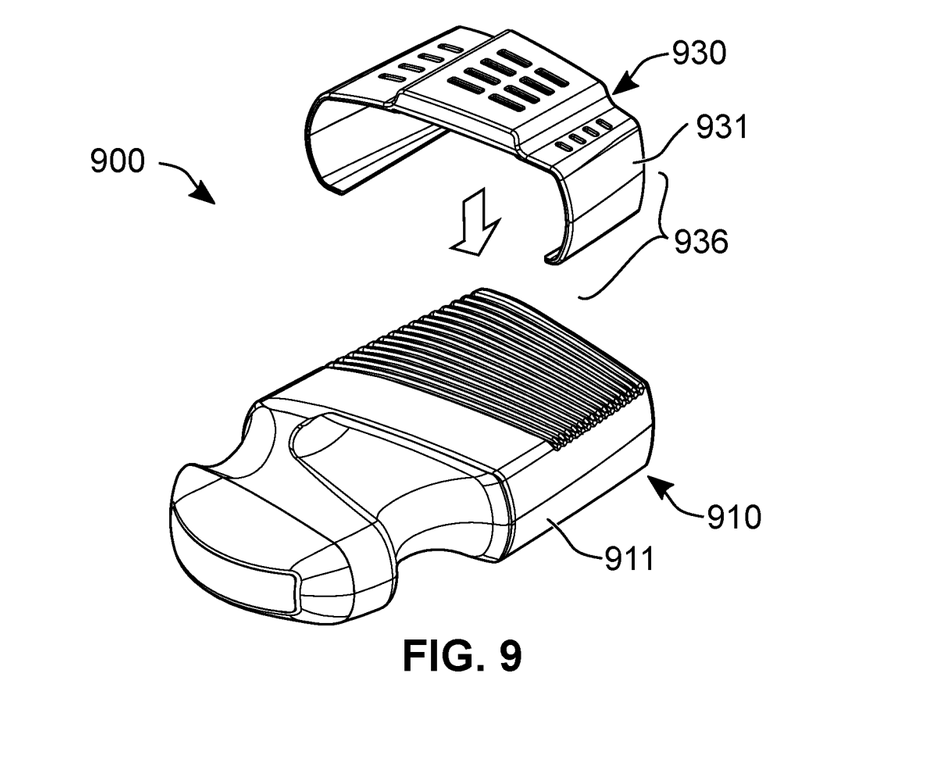

Referring to FIG. 9, shown there generally as 900 is a perspective view of another alternative embodiment of the present invention, where the active cooling unit is powered independently. Ultrasound imaging system 900 may include an ultrasound imaging apparatus 910 and a detachable active cooling unit 930 Like the example cooling units 130 discussed above, the active cooling unit 930 may have a body portion 931 that is formed with a clip portion 936 for securing around the shell 911 of the ultrasound imaging apparatus 910.

However, unlike the ultrasound imaging apparatus 110 discussed above, the ultrasound imaging apparatus 910 may be configured to not have a connector 122 for supplying power to the cooling unit 930. For example, this may simplify design or manufacturing of the ultrasound imaging apparatus 910. Additionally or alternatively, this may allow cooling units 930 to be interoperable with configurations of the ultrasound imaging apparatus without connector 122. Since the imaging apparatus may be configured without connector 122, the cooling unit 930 may similarly be configured to not have a corresponding connector 132 (as shown earlier in FIG. 3).

Instead, in the embodiment of FIG. 9, the active cooling unit 930 may include an internal power source such as a battery. The battery may provide power to the active cooling element 140 (as shown in FIG. 1) to help remove heat from ultrasound imaging apparatus 910. In various embodiments, the internal battery may be rechargeable or single-use. In various embodiments, the internal battery may be removable or non-removable. In various embodiments, the cooling unit 930 may be provided with a switch that allows for the activation and/or deactivation of the active cooling element.

Figure 10:
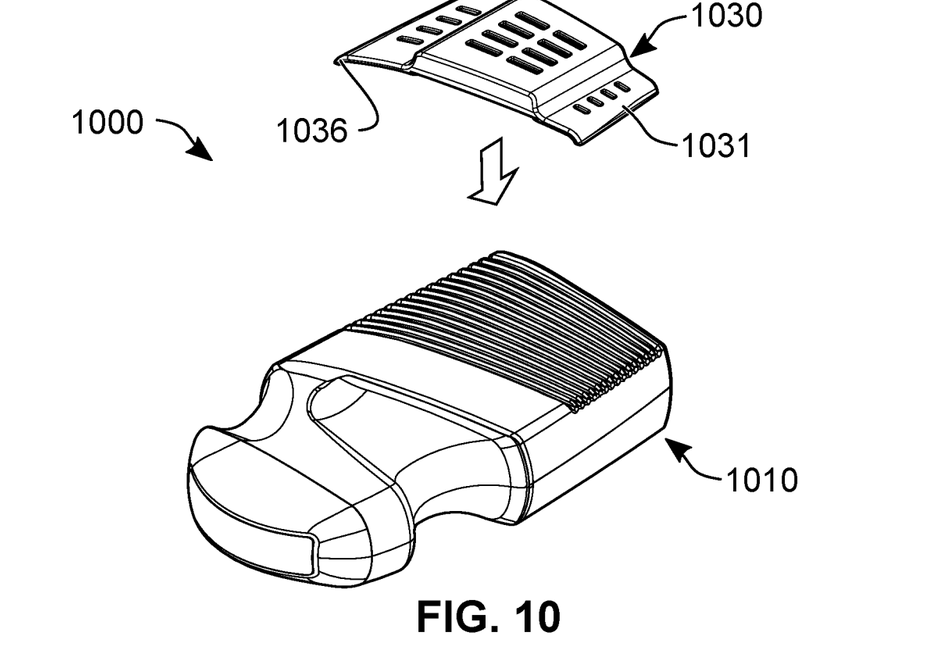

Referring to FIG. 10, shown there generally as 1000 is a perspective view of another alternative embodiment of the present invention, with both the magnetic coupling mechanism discussed above in relation to FIG. 8 and an internally powered active cooling element discussed above in relation to FIG. 9. An ultrasound imaging system 1000 may include an ultrasound imaging apparatus 1010 and a detachable active cooling unit 1030. The active cooling unit 1030 may include a housing 1031 which has at least one magnetic fastener 1036. Various configurations of coupling can be used as described in FIG. 8 above. The active cooling unit 1030 may also be self-powered, in a manner like how the active cooling unit 930 discussed above was internally powered. Accordingly, the ultrasound imaging apparatus 1010 and the active cooling unit 1030 may not be provided with respective connectors 122/132 (as shown in FIG. 1)

Figure 11:
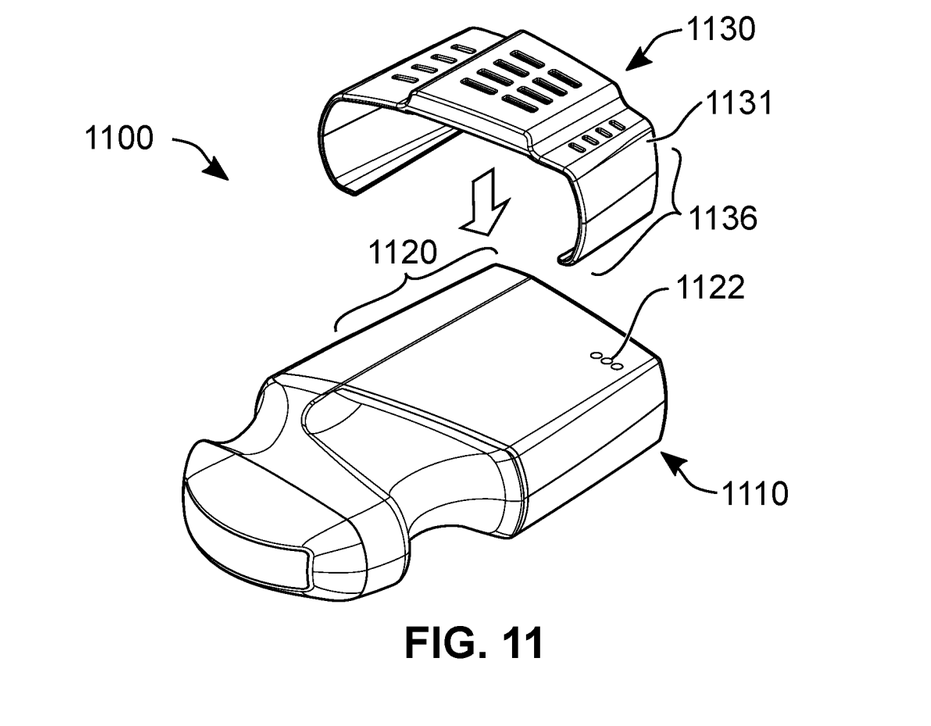

Referring to FIG. 11, shown there generally as 1100 is a perspective view of another alternative embodiment of the present invention that has a different configuration of a heat dissipater. In various embodiments discussed above, the cooling unit 130 has been shown as being coupled to ultrasound imaging apparatus with finned heat dissipaters 220 (as shown in FIG. 2A). However, such fins 220 may not be present in various embodiments. For example, as shown in FIG. 11, the heat dissipating portion 1120 of ultrasound imaging apparatus 1110 may be a surface that is substantially smooth (e.g., without fins). Even without fins, the operation of the active cooling unit 1130 to project air towards and/or away from the relatively smooth surface 1120 may still provide a cooling effect on the ultrasound imaging apparatus 1110.

The embodiment illustrated in FIG. 11 is shown as having a housing 1131 that incorporates a clip portion 1136. Also, the ultrasound imaging apparatus 1110 in FIG. 11 is shown as having a connector portion 1122. However, the various potential modifications discussed herein (e.g., magnetic coupling, self-powered without connectors 1122) may also be made to the embodiment of FIG. 11.

Referring again to FIGS. 3, 5, and 6, the example illustrated embodiments are shown as having three (3) pins 333, 334, 335 on the connector 132 of the cooling unit 130, with three (3) corresponding target pins provided on the ultrasound imaging apparatus 110. In various embodiments, there are a different number of pins provided on the connectors 122, 132 connecting the active cooling unit 130 to the ultrasound imaging apparatus 110. For example, in some embodiments, there may be only two (2) pins provided on the connectors 122, 132. This may be the case if the only two pins are provided (e.g., when activated, a live pin and a neutral pin), but the detector pin 524 (as shown in FIG. 5) is not provided. In these embodiments, the activation/deactivation of the active cooling element may be based on a suitable switch that is not contingent on the identification of a compatible cooling unit 130.

In other embodiments, there may be only a single pin provided on the connectors 122, 132 connecting the active cooling unit 130 to the ultrasound imaging apparatus 110. For example, this may be the case if the active cooling unit 130 is self-powered, and only the detector pin 524 and corresponding identity interface pin is provided to determine of an attached cooling unit 130 is compatible. In these embodiments, the ultrasound imaging apparatus 110 may be configured to not allow imaging to proceed if a non-compatible cooling unit 130 is determined to be attached.

In some embodiments, active cooling unit 130 may receive power from ultrasound imaging apparatus 110 without the use of a conductor-based (e.g., wired) electrical connection. For example, various conventionally known or future-developed wireless power transfer techniques may be used provide power to active cooling unit 130. For example, inductive coupling, capacitive coupling, and/or magnetodynamic coupling may be used to transfer power from ultrasound imaging apparatus 110 to active cooling unit 130 to power active cooling element 140.

Although the active cooling element 140 has generally been described herein as being provided in the form of fan 340, other types of active cooling element are possible. Various conventionally known or future developed active cooling elements may be used to remove heat from the ultrasound imaging apparatus 110. For example, a thermoelectric cooler or a refrigeration cycle-based heat pump may be used alone or in combination to provide active cooling.

As illustrated herein, the ultrasound imaging apparatus 110 is shown as being in the form of a wireless ultrasound scanner that may connect via wireless communication protocols to a suitable display for displaying the ultrasound image data generated from the scanner. However, the present embodiments can be practiced with ultrasound imaging apparatus of any types, whether wired or wireless. By providing a cooling unit 130 that either draws power from the ultrasound imaging apparatus 110 or is self-powered (as discussed above), the cooling unit 130 can provide the advantages of active cooling while still being cordless. This may facilitate ease of attachment and portability for the cooling unit 130 for either wired or wireless ultrasound imaging apparatus 110. This may also allow for scanning of longer duration for ultrasound imaging apparatus 110 that is either wired or wireless.

In various embodiments, the ultrasound imaging apparatus 110 may be configured to control activation of a cooling unit 130 based on temperature sensors provided within the ultrasound imaging apparatus 110. For example, an ultrasound operator may wish to perform an ultrasound examination in a location with a high ambient temperature. The ultrasound operator may attach the active cooling unit 130 to the ultrasound imaging apparatus 110 and begin scanning. When the active cooling unit 130 is attached, an electrical connection may be formed, which may allow a processor within the ultrasound imaging apparatus 110 to detect the cooling unit's 130 presence and control power to it. The ultrasound imaging apparatus 110 may be provided with temperature sensor(s) that the processor may monitor. If the temperature exceeds a predetermined value, the processor may turn on the active cooling unit 130. When powered on, the active cooling element (e.g., a fan) may force air past a heat dissipating portion of the ultrasound imaging apparatus 110, and enhance the cooling beyond natural convection. This may allow the ultrasound operator to continue scanning in a situation where the temperature sensor may otherwise need to stop the ultrasound imaging apparatus 110 from scanning due to high temperatures.

In various embodiments, the ultrasound imaging apparatus 110 may adjust imaging parameters based on the status of attachment of cooling unit 130. Since an attached cooling unit 130 may allow the ultrasound imaging apparatus 110 to operate with a higher processing load that generates more heat, these adjustments may increase image quality or imaging performance when the cooling unit 130 is attached. Correspondingly, the ultrasound imaging apparatus 110 may decrease image quality or imaging performance when the cooling unit 130 is detached (e.g., to lower processing load and thus, heat generation). For example, a frame acquisition rate, a line density, or other imaging parameter may be increased to provide better image quality when the cooling unit 130 is attached.

In various embodiments, the identity interface may provide additional information to the imaging apparatus 110. For example, the identity interface may be configured to provide information about the heat dissipating capacity of the cooling unit 130. The heat dissipation information may be used by the imaging apparatus 110 to change imaging parameters to achieve a desired run time. In another example, the heat dissipating capacity information may be used by the imaging apparatus 110 to provide an estimated run time to the user.

In various embodiments, the active cooling unit 130 may be provided in different configurations or forms having varying types of active cooling elements 140. For example, these different configurations may be recognized and/or differentiated by the ultrasound imaging apparatus 110 using the identity interface. In example embodiment, one configuration of the active cooling unit 130 may have a small, lightweight fan configured to remove a relatively small amount of heat (while consuming relatively small amount of power); and a second configuration of the cooling unit 130 may have a larger, heavier (and potentially bulkier) fan capable of removing more heat but drawing more power. The ultrasound imaging apparatus 110 may distinguish between the two active cooling units and provide different estimates of allowable run-time, and/or activate different imaging modes as described above.

In some cases, the ultrasound imaging apparatus 110 may continue to increase in temperature even after the cooling unit 130 is running. If a second predetermined temperature threshold is detected, the ultrasound imaging apparatus 110 may be configured to alert the ultrasound operator (e.g., via a light-emitting diode (LED), audio, or through a suitable display device) that the ultrasound imaging apparatus 110 may stop scanning. In various embodiments, the active cooling unit 130 may continue running after scanning has been stopped to cool the ultrasound imaging apparatus 110. The ultrasound operator may be alerted when the imaging apparatus is cool enough to resume scanning.

When the ultrasound operator wishes to perform an exam that is relatively short in duration, they may simply remove the detachable cooling unit 130 and scan normally.

While a number of exemplary aspects and embodiments have been discussed above, those of skill in the art will recognize that may be certain modifications, permutations, additions and sub-combinations thereof. While the above description contains many details of example embodiments, these should not be construed as essential limitations on the scope of any embodiment. Many other ramifications and variations are possible within the teachings of the various embodiments.

Interpretation of Terms

Unless the context clearly requires otherwise, throughout the description and the claims:
- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;
- the singular forms "a", "an", and "the" also include the meaning of any appropriate plural forms.

Unless the context clearly requires otherwise, throughout the description and the claims:
  Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. An ultrasound imaging system comprising:
    an ultrasound imaging scanner operable to acquire ultrasound image data, the ultrasound imaging scanner comprising first electrical connection points on a handheld portion of the ultrasound imaging scanner; and
    a cordless cooling unit configured to detachably couple to the handheld portion of the ultrasound imaging scanner, the cordless cooling unit comprising second electrical connection points, wherein when the cordless cooling unit is coupled to the handheld portion of the ultrasound imaging scanner, the second electrical connection points directly contact the first electrical connection points to form an electrical connection between the first electrical connection points on the handheld portion of the ultrasound imaging scanner and the second electrical connection points on the cordless cooling unit;
    wherein the cordless cooling unit comprises an active cooling element to remove heat from the ultrasound imaging scanner, and when the cordless cooling unit is coupled to the handheld portion of the ultrasound imaging scanner, electricity for powering the active cooling element is supplied through the electrical connection formed between the first electrical connection points on the handheld portion of the ultrasound imaging scanner and the second electrical connection points on the cordless cooling unit.

2. The ultrasound imaging system of claim 1, wherein the ultrasound imaging scanner further comprises at least one sensor to detect when the cordless cooling unit is coupled.

3. The ultrasound imaging system of claim 2, wherein the at least one sensor comprises at least a portion of a resistor voltage divider network.

4. The ultrasound imaging system of claim 1, wherein the ultrasound imaging scanner comprises an external surface and the active cooling element comprises a fan, and wherein said fan is configured to direct air onto or from said external surface.

5. The ultrasound imaging system of claim 1, wherein the cordless cooling unit comprises at least one fastener to perform the detachable coupling.

6. The ultrasound imaging system of claim 1, wherein the ultrasound imaging scanner comprises a shell and wherein said shell protects from ingress into an interior of the ultrasound imaging scanner.

7. The ultrasound imaging system of claim 1, wherein the cooling unit further comprises an internal battery for powering the active cooling element.

8. The ultrasound imaging system of claim 1, wherein the fastener is formed with a housing of the cordless cooling unit, and the housing comprises at least one clip for performing the detachable coupling.

9. The ultrasound imaging system of claim 2, wherein an identity interface is provided on the cordless cooling unit, and the identity interface is read through the at least one sensor to detect when the cordless cooling unit is coupled.

10. The ultrasound imaging system of claim 9, wherein the ultrasound imaging scanner is configured to determine whether the coupled cordless cooling unit is compatible based on whether a reading of the identity interface matches an expected reading; and the ultrasound imaging scanner is further configured to limit or stop the electricity for powering the active cooling element supplied through the electrical connection when the cordless cooling unit is detected to be not compatible.

* * * * *